(12) United States Patent
Schabbach et al.

(10) Patent No.: US 10,173,001 B2
(45) Date of Patent: Jan. 8, 2019

(54) DRIVE MECHANISM FOR A NEEDLE INSERTION ARRANGEMENT

(71) Applicant: Sanofi-Aventis Deutschland GMBH, Frankfurt am Main (DE)

(72) Inventors: Michael Schabbach, Frankfurt am Main (DE); Meinolf Werner, Worms (DE); Olaf Zeckai, Weinheim (DE); Philippe Nzike, Frankfurt am Main (DE)

(73) Assignee: Sanofi-Aventis Deutschland, Frankfurt am Main (DE)

( * ) Notice: Subject to any disclaimer, the term of this patent is extended or adjusted under 35 U.S.C. 154(b) by 214 days.

(21) Appl. No.: 14/916,682

(22) PCT Filed: Sep. 2, 2014

(86) PCT No.: PCT/EP2014/068601
§ 371 (c)(1),
(2) Date: Mar. 4, 2016

(87) PCT Pub. No.: WO2015/032747
PCT Pub. Date: Mar. 12, 2015

(65) Prior Publication Data
US 2016/0193405 A1    Jul. 7, 2016

(30) Foreign Application Priority Data
Sep. 5, 2013 (EP) .................................. 13183156

(51) Int. Cl.
*A61M 5/158* (2006.01)
*A61M 5/32* (2006.01)
*A61M 5/46* (2006.01)

(52) U.S. Cl.
CPC .......... *A61M 5/158* (2013.01); *A61M 5/3287* (2013.01); *A61M 5/46* (2013.01); *A61M 2005/1585* (2013.01)

(58) Field of Classification Search
CPC .......... A61M 2005/1585; A61M 5/158; A61M 37/0076; A01K 11/005; D05B 55/00;
(Continued)

(56) References Cited

U.S. PATENT DOCUMENTS

2010/0228195 A1    9/2010 Ulrich et al.

FOREIGN PATENT DOCUMENTS

CN    103128025    6/2013
DE    202009003050    8/2010
(Continued)

OTHER PUBLICATIONS

International Search Report and Written Opinion in International Application No. PCT/EP2014/068601, dated Sep. 17, 2014, 9 pages.
(Continued)

*Primary Examiner* — Laura A Bouchelle
*Assistant Examiner* — Tasnim Mehjabin Ahmed
(74) *Attorney, Agent, or Firm* — Fish & Richardson P.C.

(57) ABSTRACT

The invention relates to a drive mechanism (9) for a needle insertion arrangement (1), the drive mechanism (9) comprising: —an actuator (5), —a needle retainer (7) adapted to retain an injection needle (2) and linearly movable in a distal direction (D) and a proximal direction (P) for moving an injection needle (2), —a cam (17) arranged on or coupled to the needle retainer (7), —a guide curve (16) adapted to be rotated by the actuator (5) about an axis (12) aligned in the distal direction (D) and the proximal direction (P) and adapted to engage the cam (17), wherein the guide curve
(Continued)

(16) comprises a sloped section (16.2) such that the needle retainer (7) is moved on rotation of the guide curve (16).

20 Claims, 6 Drawing Sheets

(58) Field of Classification Search
 CPC ........ D05B 55/02; D05B 55/04; D05B 55/06; D05B 55/10; D05B 55/12; D05B 55/14; D05B 55/16
 See application file for complete search history.

(56) References Cited

FOREIGN PATENT DOCUMENTS

| EP | 1669028 | 6/2006 |
|---|---|---|
| WO | WO2009/125879 | 10/2009 |
| WO | WO2011/010764 | 1/2011 |

OTHER PUBLICATIONS

International Preliminary Report on Patentability in International Application No. PCT/EP2014/068601, dated Mar. 8, 2016, 6 pages.
"Pen-injectors for medical use—Part 1: Pen-injectors—Requirements and test methods," International Standard, reference number: ISO 11608-1:2000(E), first edition Dec. 15, 2000, 32 pages.

DRIVE MECHANISM FOR A NEEDLE INSERTION ARRANGEMENT

CROSS-REFERENCE TO RELATED APPLICATIONS

This application is a U.S. national stage application under 35 USC § 371 of International Application No. PCT/EP2014/068601, filed on Sep. 2, 2014, which claims priority to European Patent Application No. 13183156.2, filed on Sep. 5, 2013, the entire contents of which are incorporated herein by reference.

TECHNICAL FIELD

The invention relates to a drive mechanism for a needle insertion arrangement.

BACKGROUND OF THE INVENTION

Administering an injection is a process which presents a number of risks and challenges for users and healthcare professionals, both mental and physical. During manual insertion of an injection needle into an injection site, e.g. the skin of a patient, it may be difficult to avoid tilting and bending of the needle and the insertion may be slow thus causing pain.

There remains a need for an improved drive mechanism for a needle insertion arrangement.

SUMMARY OF THE INVENTION

Aspects of the present invention can include providing an improved drive mechanism for a needle insertion mechanism.

The aspects can be implemented by a drive mechanism for a needle insertion arrangement according to claim 1.

Exemplary embodiments of the invention are given in the dependent claims.

According to the invention a drive mechanism for a needle insertion arrangement comprises:
- an actuator,
- a needle retainer adapted to retain an injection needle and linearly movable in a distal direction and a proximal direction for moving an injection needle,
- a cam arranged on or coupled to the needle retainer,
- a guide curve adapted to be rotated by the actuator about an axis aligned in the distal direction and the proximal direction and adapted to engage the cam, wherein the guide curve comprises a sloped section such that the needle retainer is moved on rotation of the guide curve.

When the drive mechanism is applied in a needle insertion arrangement limited space requirements are achieved thus allowing for low profile injection devices with a high wearing comfort. The insertion arrangement achieves high speed needle movements and exact needle guidance thus reducing pain for the patients when inserting and retracting the needle and increasing consumer acceptance and satisfaction. The low part count of the insertion arrangement and the low requirements for electronic equipment allow for an increased mechanical robustness and low manufacturing costs. The insertion arrangement is a fault-tolerant system. The movement of the needle may be customized to the respective application by modifying the curve geometry. In an exemplary embodiment the actuator may be replaced by a handle for manually operating the drive mechanism. The drive mechanism is permanently positively coupled to the needle. When using a sensor for detecting whether the needle is in the extended position, this allows for ensuring that an injection is only performed when the needle is in the extended position, e.g. inserted in an injection site at insertion depth.

In an exemplary embodiment the guide curve further comprises:
- a proximal section with a zero pitch, and
- a distal section with a zero pitch, wherein the sloped section connects the proximal section with the distal section.

As long as the cam is located in the zero pitch proximal section the needle retainer and the needle remain in the retracted position while the actuator is permitted to reach its nominal speed. Due to the zero pitch distal section of the guide curve the actuator is allowed to run out after having rapidly moved the needle retainer and the needle.

In an exemplary embodiment the guide curve is arranged on or in a shaft rotatable about the axis.

In an exemplary embodiment the guide curve is arranged as a notch milled into the shaft.

In an exemplary embodiment the guide curve is arranged as a helically wound rod arranged about the axis and or about a linear guide.

In an exemplary embodiment the cam is adapted to engage the rod

In an exemplary embodiment the cam is adapted to engage in the space between neighbouring windings of the rod.

In an exemplary embodiment the actuator is arranged as an electrical motor coupled to the guide curve.

In an exemplary embodiment the actuator is directly coupled to the guide curve.

In an exemplary embodiment a gear is arranged for coupling the actuator to the guide curve.

In an exemplary embodiment the gear is arranged as a belt drive.

In an exemplary embodiment the gear is arranged as a spur gear.

In an exemplary embodiment the gear is arranged as a worm gear.

In an exemplary embodiment at least one linear guide is arranged for guiding the needle retainer.

The drive mechanism may be arranged in an insertion arrangement for moving an injection needle between a retracted position and an extended position, comprising a disposable unit, comprising a needle base, to which the needle is fixed, wherein the needle retainer is adapted to retain the needle base.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
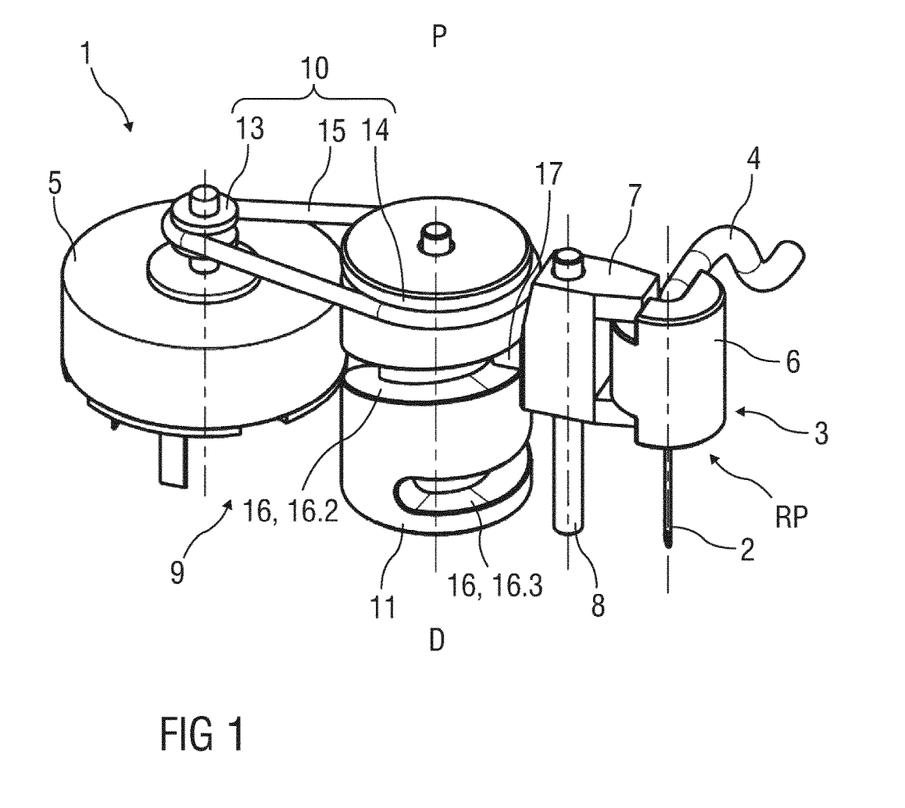
FIG. 1 is a schematic perspective view of a first exemplary embodiment of an insertion arrangement for inserting and retracting an injection needle.

FIG. 1 is a schematic perspective view of a first exemplary embodiment of an insertion arrangement 1 for automatically or semi-automatically inserting an injection needle 2 into an injection site. The arrangement 1 may be applied in medicament pumps, e.g. insulin pumps which may be permanently worn on the body.

The injection needle 2 is part of a disposable unit 3, further comprising a tube 4 for establishing a fluid communication of the needle 2 with a drug container (not illustrated) and comprising a needle base 6, to which the injection needle 2 may be fixed for mechanically connecting the needle 2 to a drive mechanism 9 of an injection unit (not illustrated). The needle base 6 is inserted in a needle retainer 7 which is arranged to be moved in a distal direction D and/or a proximal direction P along a linear guide 8. This linear movement corresponds to insertion of the needle 2 into the injection site, e.g. subcutaneous body tissue and removal from the injection site, respectively.

The drive mechanism 9 for the needle 2 comprises an actuator 5, e.g. an electrical motor, coupled through a gear 10 to a cylindrical shaft 11 rotatable about an axis 12 aligned in the distal direction D and the proximal direction P, such that the actuator 5 can rotate the shaft 11. In the illustrated embodiment the gear 10 comprises a drive pulley 13 on the actuator 5, an output pulley 14 on or integrated with the shaft 11 and a belt 15 engaging the drive pulley 13 to the output pulley 14. A thread-like guide curve 16 is arranged in or on the shaft 11. The needle retainer 7 comprises a cam 17 adapted to engage the guide curve 16. If the shaft 11 is rotated the guide curve 16 is moved along the cam 17 thus moving the needle retainer 7 and the needle 2 in the distal direction D or the proximal direction P depending on a rotational direction of the shaft 11. The guide curve 16 comprises a proximal section 16.1 with zero pitch (best seen in FIG. 2), followed by a sloped section 16.2 with a relatively high pitch and a distal section 16.3 with zero pitch.

Figure 2:
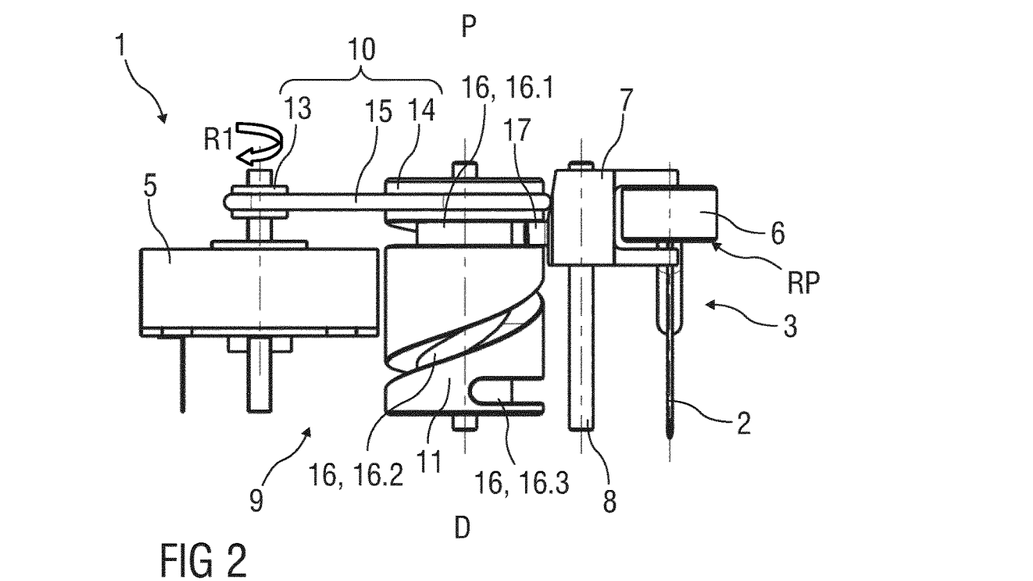
FIG. 2 is a schematic side view of the first embodiment of the insertion arrangement in an initial position, wherein the needle is in a retracted position.

A sequence of operation of the insertion arrangement 1 is as follows:

FIG. 2 is a schematic side view of the first embodiment of the insertion arrangement 1 in an initial position. The disposable unit 3 with the needle base 6, the needle 2 and the tube 4 has been inserted in the forked needle retainer 7. The needle retainer 7 and the needle 2 are in a retracted position RP. The cam 17 is located in the proximal section 16.1. The actuator 5 starts rotating in a first rotational direction R1, thus also causing the shaft 11 to rotate in the first rotational direction R1. As long as the cam 17 is located in the zero pitch proximal section 16.1 the needle retainer 7 and the needle 2 remain in the retracted position RP.

Figure 3:
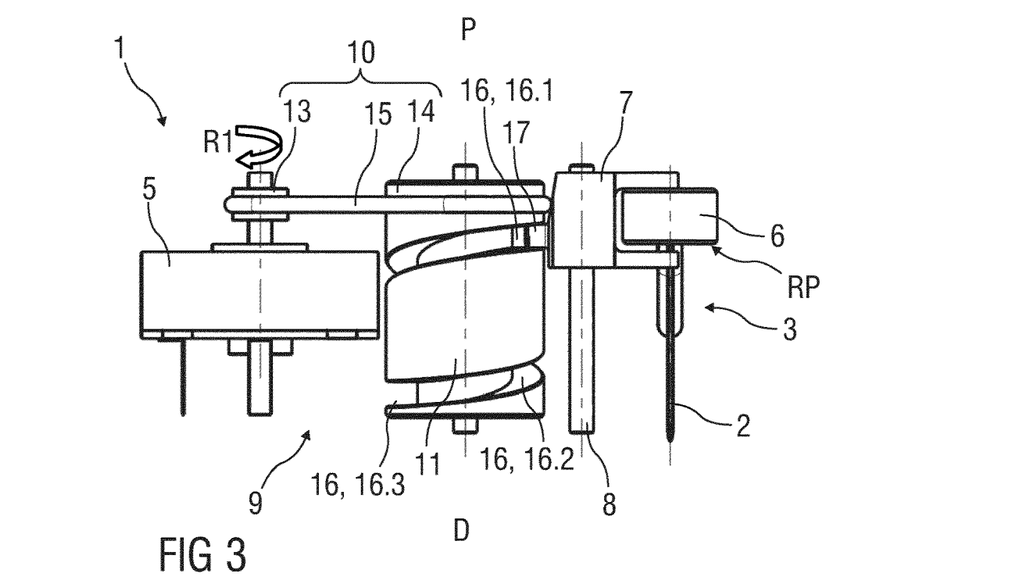
FIG. 3 is a schematic side view of the first embodiment of the insertion arrangement with a cam entering a sloped section of a guide curve.

FIG. 3 is a schematic side view of the first embodiment of the insertion arrangement 1 with the cam 17 entering the sloped section 16.2 of the guide curve 16. The actuator 5 and the shaft 11 have reached their nominal speeds. Due to the pitch of the guide curve 16 being greater than zero at the beginning of the sloped section 16.2 the needle retainer 7 and the needle 2 start moving in the distal direction D.

Figure 4:
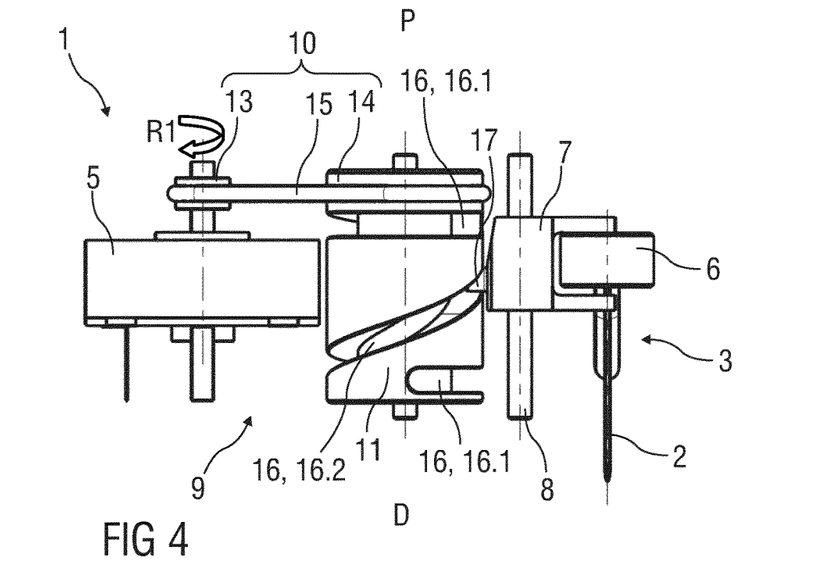
FIG. 4 is a schematic side view of the first embodiment of the insertion arrangement with the cam in the sloped section of the guide curve.

FIG. 4 is a schematic side view of the first embodiment of the insertion arrangement 1 with the cam 17 in the sloped section 16.2 of the guide curve 16. The actuator 5 and the shaft 11 continue rotating with their nominal speeds. Due to the pitch of the guide curve 16 having reached its maximum in the sloped section 16.2 the needle retainer 7 and the needle 2 move in the distal direction D with high speed.

Figure 5:
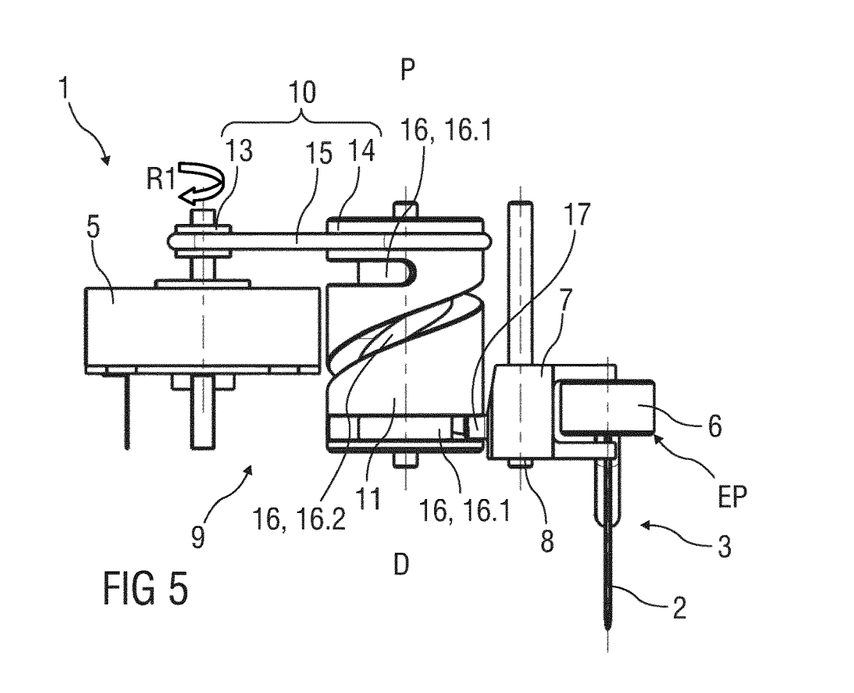
FIG. 5 is a schematic side view of the first embodiment of the insertion arrangement with the cam entering a distal section of the guide curve, wherein the needle is in an extended position.

FIG. 5 is a schematic side view of the first embodiment of the insertion arrangement 1 with the cam 17 entering the distal section 16.3 of the guide curve 16. The actuator 5 and the shaft 11 continue rotating with their nominal speeds. Due to the pitch of the guide curve 16 decreasing to zero the needle retainer 7 and the needle 2 slowly come to a standstill and reach an extended position EP. The needle 2 is in its insertion depth within an injection site, e.g. subcutaneous body tissue.

Figure 6:
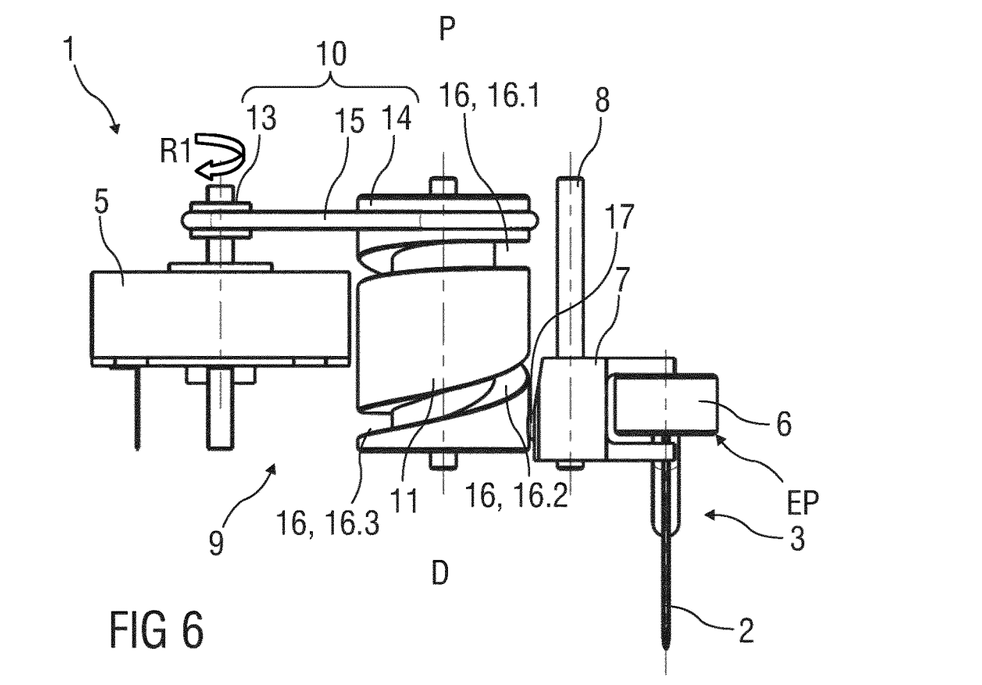
FIG. 6 is a schematic side view of the first embodiment of the insertion arrangement with the cam in the distal section of the guide curve and the needle in the extended position.

FIG. 6 is a schematic side view of the first embodiment of the insertion arrangement 1 with the cam 17 in the distal section 16.3 of the guide curve 16. The actuator 5 and the shaft 11 run out. Due to the zero pitch of the guide curve 16 the needle retainer 7 and the needle 2 remain in the extended position EP. In order to stop the actuator 5 a sensor (not illustrated) may be arranged to detect the needle 2 or the needle retainer 7 reaching the extended position EP.

Subsequently, the needle 2 may be retracted into the retracted position RP in an analogous manner by reversing the rotational direction of the actuator 5.

The characteristics of the movement of the needle retainer 7 and the needle 2 may be varied by altering the geometry of the guide curve 16. In the illustrated embodiment the guide curve 16 comprises a section with a relatively high pitch in the middle of the shaft 11 and sections with zero pitch at the proximal end and the distal end of the guide curve 16. This allows for a relatively slow start of the needle extension for piercing the injection site and a consecutive fast continuation of the needle extension for approaching the insertion depth and a final slow stop of the needle extension.

Figure 7:
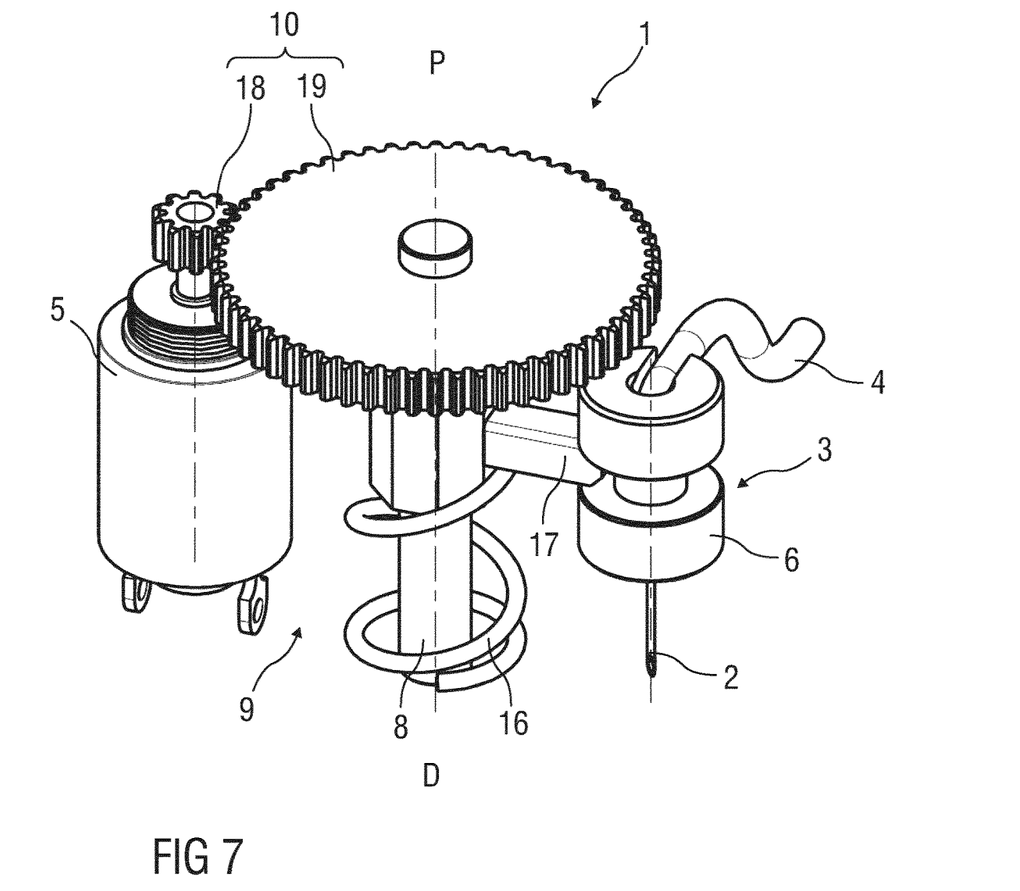
FIG. 7 is a schematic perspective view of a second exemplary embodiment of the insertion arrangement.

FIG. 7 is a schematic perspective view of a second exemplary embodiment of an insertion arrangement 1. The second embodiment functionally corresponds to the first embodiment; however instead of the guide curve 16 in the shaft 11 of the first embodiment the second embodiment comprises a guide curve 16 in the shape of a helically wound rod arranged about the linear guide 8. A cam 17 on the needle retainer 7 is adapted to engage the guide curve 16. The cam 17 may be adapted to engage the rod or the space between neighbouring windings of the rod. Furthermore, in the second embodiment the gear 10 is arranged as a spur gear with a first gear wheel 18 coupled to the actuator 5 and engaged to a second gear wheel 19 coupled to the guide curve 16. The operation of the second embodiment of the insertion arrangement 1 is analogous to the first embodiment. However, the spur gear 10 reverses the rotational direction of the actuator 5 with respect to the guide curve 16.

Figure 8:
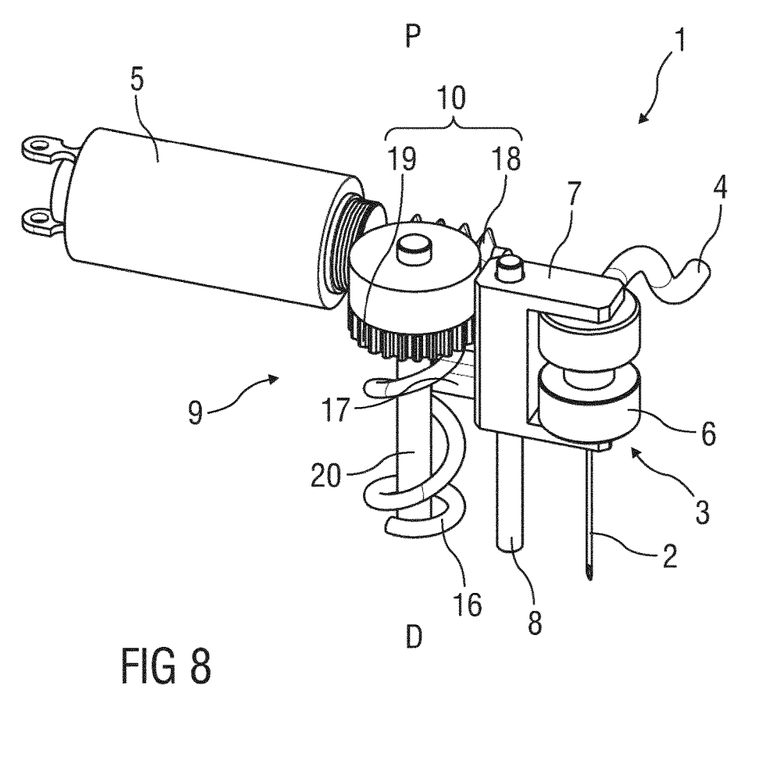
FIG. 8 is a schematic perspective view of a third exemplary embodiment of the insertion arrangement.

FIG. 8 is a schematic perspective view of a third exemplary embodiment of an insertion arrangement 1. The second embodiment functionally corresponds to the first and the second embodiment; however instead of the guide curve 16 in the shaft 11 of the first embodiment the third embodiment comprises a guide curve 16 in the shape of a helically wound rod arranged about a second linear guide 20 arranged in parallel with the linear guide 8. A cam 17 on the needle retainer 7 is adapted to engage the guide curve 16. The cam 17 may be adapted to engage the rod or the space between neighbouring windings of the rod. Furthermore, in the third embodiment the gear 10 is arranged as a worm gear with a first gear wheel 18 arranged as a worm wheel coupled to the actuator 5 and engaged to a second gear wheel 19 coupled to the guide curve 16. The operation of the third embodiment of the insertion arrangement 1 is analogous to the first and second embodiment. However, the worm gear 10 requires that the actuator 5 rotates about an axis aligned at right angles with respect to the linear guide 8.

In another alternative embodiment the actuator 5 may be directly coupled to the shaft 11 without an intermediate gear 10.

Those of skill in the art will understand that the gear 10 of any one of the embodiments may be applied in any other one of the illustrated embodiments. Likewise, the guide curve 16 of any one of the illustrated embodiments may be applied in any other one of the illustrated embodiments.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCE 1 insertion arrangement
2 injection needle
3 disposable unit
4 tube
5 actuator
6 needle base
7 needle retainer
8 linear guide
9 drive mechanism
10 gear
11 shaft
12 axis
13 drive pulley
14 output pulley
15 belt
16 guide curve
16.1 proximal section
16.2 sloped section
16.3 distal section
17 cam
18 first gear wheel
19 second gear wheel
20 second linear guide
D distal direction
EP extended position
P proximal direction
R1 first rotational direction
RP retracted position

The invention claimed is:

1. Drive mechanism for a needle insertion arrangement of an injection device, the drive mechanism comprising:
   an actuator;
   a needle retainer adapted to retain an injection needle, the needle retainer linearly movable in a distal direction (D) and a proximal direction (P) for moving an injection needle;
   a cam arranged on or coupled to the needle retainer; and
   a guide curve adapted to be rotated by the actuator about an axis aligned in the distal direction (D) and the proximal direction (P) and adapted to engage the cam, wherein the guide curve comprises a sloped section such that the needle retainer is moved on rotation of the guide curve, wherein the guide curve further comprises:
     a proximal section with a zero pitch, and
     a distal section with a zero pitch, wherein the sloped section connects the proximal section with the distal section.

2. Drive mechanism according to claim 1, wherein the guide curve is arranged on or in a shaft rotatable about the axis.

3. Drive mechanism according to claim 2, wherein the guide curve is arranged as a notch milled into the shaft.

4. Drive mechanism according to claim 1, wherein the guide curve is arranged as a helically wound rod arranged about the axis and or about a linear guide.

5. Drive mechanism according to claim 4, wherein the cam is adapted to engage the rod.

6. Drive mechanism according to claim 4, wherein the cam is adapted to engage in the space between neighboring windings of the rod.

7. Drive mechanism according to claim 1, wherein the actuator is arranged as an electrical motor coupled to the guide curve.

8. Drive mechanism according to claim 1, wherein the actuator is directly coupled to the guide curve.

9. Drive mechanism according to claim 1, wherein a gear is arranged for coupling the actuator to the guide curve.

10. Drive mechanism according to claim 9, wherein the gear is arranged as a belt drive.

11. Drive mechanism according to claim 9, wherein the gear is arranged as a spur gear.

12. Drive mechanism according to claim 9, wherein the gear is arranged as a worm gear.

13. Drive mechanism according to claim 1, wherein at least one linear guide is arranged for guiding the needle retainer.

14. Insertion arrangement for moving an injection needle between a retracted position (RP) and an extended position (EP), the insertion arrangement comprising:
   a disposable unit comprising a needle base to which the needle is fixed; and
   a drive mechanism comprising:
     an actuator;
     a needle retainer adapted to retain an injection needle, the needle retainer linearly movable in a distal direction (D) and a proximal direction (P) for moving an injection needle;
     a cam arranged on or coupled to the needle retainer; and
     a guide curve adapted to be rotated by the actuator about an axis aligned in the distal direction (D) and the proximal direction (P) and adapted to engage the cam, wherein the guide curve comprises a sloped section such that the needle retainer is moved on rotation of the guide curve, wherein the guide curve further comprises:
       a proximal section with a zero pitch, and
       a distal section with a zero pitch, wherein the sloped section connects the proximal section with the distal section,
     wherein the needle retainer is adapted to retain the needle base.

15. The insertion arrangement according to claim 14, wherein the guide curve is arranged on or in a shaft rotatable about the axis.

16. The insertion arrangement according to claim 15, wherein the guide curve is arranged as a notch milled into the shaft.

17. The insertion arrangement according to claim 14, wherein the guide curve is arranged as a helically wound rod arranged about the axis and or about a linear guide.

18. The insertion arrangement according to claim 17, wherein the cam is adapted to engage the rod.

19. The insertion arrangement according to claim 17, wherein the cam is adapted to engage in the space between neighboring windings of the rod.

20. An auto-injector comprising:
an insertion arrangement for moving an injection needle between a retracted position (RP) and an extended position (EP), the insertion arrangement comprising:
   a disposable unit comprising a needle base to which the needle is fixed; and
   a drive mechanism comprising:
      an actuator;
      a needle retainer adapted to retain an injection needle, the needle retainer linearly movable in a distal direction (D) and a proximal direction (P) for moving an injection needle;
      a cam arranged on or coupled to the needle retainer; and
      a guide curve adapted to be rotated by the actuator about an axis aligned in the distal direction (D) and the proximal direction (P) and adapted to engage the cam, wherein the guide curve comprises a sloped section such that the needle retainer is moved on rotation of the guide curve, wherein the guide curve further comprises:
         a proximal section with a zero pitch, and
      a distal section with a zero pitch, wherein the sloped section connects the proximal section with the distal section, wherein the needle retainer is adapted to retain the needle base; and
a drug container coupled to the injection needle, the drug container carrying a medicament consisting of at least one pharmaceutically active compound.

* * * * *

UNITED STATES PATENT AND TRADEMARK OFFICE
CERTIFICATE OF CORRECTION

PATENT NO. : 10,173,001 B2
APPLICATION NO. : 14/916682
DATED : January 8, 2019
INVENTOR(S) : Schabbach et al.

Page 1 of 1

It is certified that error appears in the above-identified patent and that said Letters Patent is hereby corrected as shown below:

On the Title Page

Item (73), Column 1 (Assignee), delete "Deutschland," and insert -- Deutschland GMBH, --;

In the Claims

In Column 10, Line 15, Claim 4, delete "and or" and insert -- and/or --;

In Column 11, Line 3, Claim 17, delete "and or" and insert -- and/or --.

Signed and Sealed this
Fifth Day of May, 2020

Andrei Iancu
*Director of the United States Patent and Trademark Office*